United States Patent [19]
Wilson et al.

[11] Patent Number: 5,251,625
[45] Date of Patent: Oct. 12, 1993

[54] APPARATUS AND METHOD FOR CONTROLLING TACHYARRHYTHMIA CONFIRMATION IN RESPONSE TO PATIENT HISTORY

[75] Inventors: Stephen G. Wilson, Stanmore; Anthony C. Stephens, Willoughby, both of Australia

[73] Assignee: Telectronics Pacing Systems, Inc., Englewood, Colo.

[21] Appl. No.: 898,966

[22] Filed: Jun. 12, 1992

[30] Foreign Application Priority Data

Oct. 22, 1991 [AU] Australia .................. PK9024

[51] Int. Cl.$^5$ ............................................ A61N 1/362
[52] U.S. Cl. .................................... 607/6; 607/7
[58] Field of Search ................ 128/419 PG, 419 D

[56] References Cited

U.S. PATENT DOCUMENTS

| | | | |
|---|---|---|---|
| 3,857,398 | 12/1974 | Rubin | 128/419 D |
| 4,375,817 | 3/1983 | Engle et al. | 128/419 D |
| 4,432,375 | 2/1984 | Angel et al. | 128/705 |
| 4,865,036 | 9/1989 | Chirife | 128/419 D |
| 4,869,252 | 9/1989 | Gilli | 128/419 PG |
| 4,895,151 | 1/1990 | Grevis et al. | 128/419 PG |
| 4,940,054 | 7/1990 | Grevis et al. | 128/419 PG |
| 4,969,465 | 11/1990 | Pless et al. | 128/419 PG |
| 4,971,058 | 11/1990 | Pless et al. | 128/419 PG |
| 5,065,759 | 11/1991 | Begemann et al. | 128/419 PG |
| 5,078,133 | 1/1992 | Heinz et al. | 128/419 PG |
| 5,086,772 | 2/1992 | Larnard et al. | 128/419 PG |

FOREIGN PATENT DOCUMENTS

| | | |
|---|---|---|
| 0334618 | 9/1989 | European Pat. Off. . |
| 0340045 | 11/1989 | European Pat. Off. . |
| 0358303 | 3/1990 | European Pat. Off. . |
| 0360412 | 3/1990 | European Pat. Off. . |

*Primary Examiner*—William E. Kamm
*Assistant Examiner*—George Manuel
*Attorney, Agent, or Firm*—Gottlieb, Rackman & Reisman

[57] ABSTRACT

A method and apparatus for delivering electrical therapy to the heart are disclosed. The apparatus detects and confirms the arrhythmia. However, during confirmation, if the arrhythmia is present but not too severe, it is allowed to continue in the hope that it will spontaneously revert. The arrhythmia is reconfirmed later and, if it is still present, electrical therapy is delivered to the heart. Thus, for mild arrhythmias, electrical shock therapy is withheld for a specified time period in the hope that the arrhythmia will revert spontaneously. More severe arrhythmias which are not hemodynamically sustaining are immediately electrically shocked in an effort to revert the heart back to normal sinus rhythm.

12 Claims, 2 Drawing Sheets

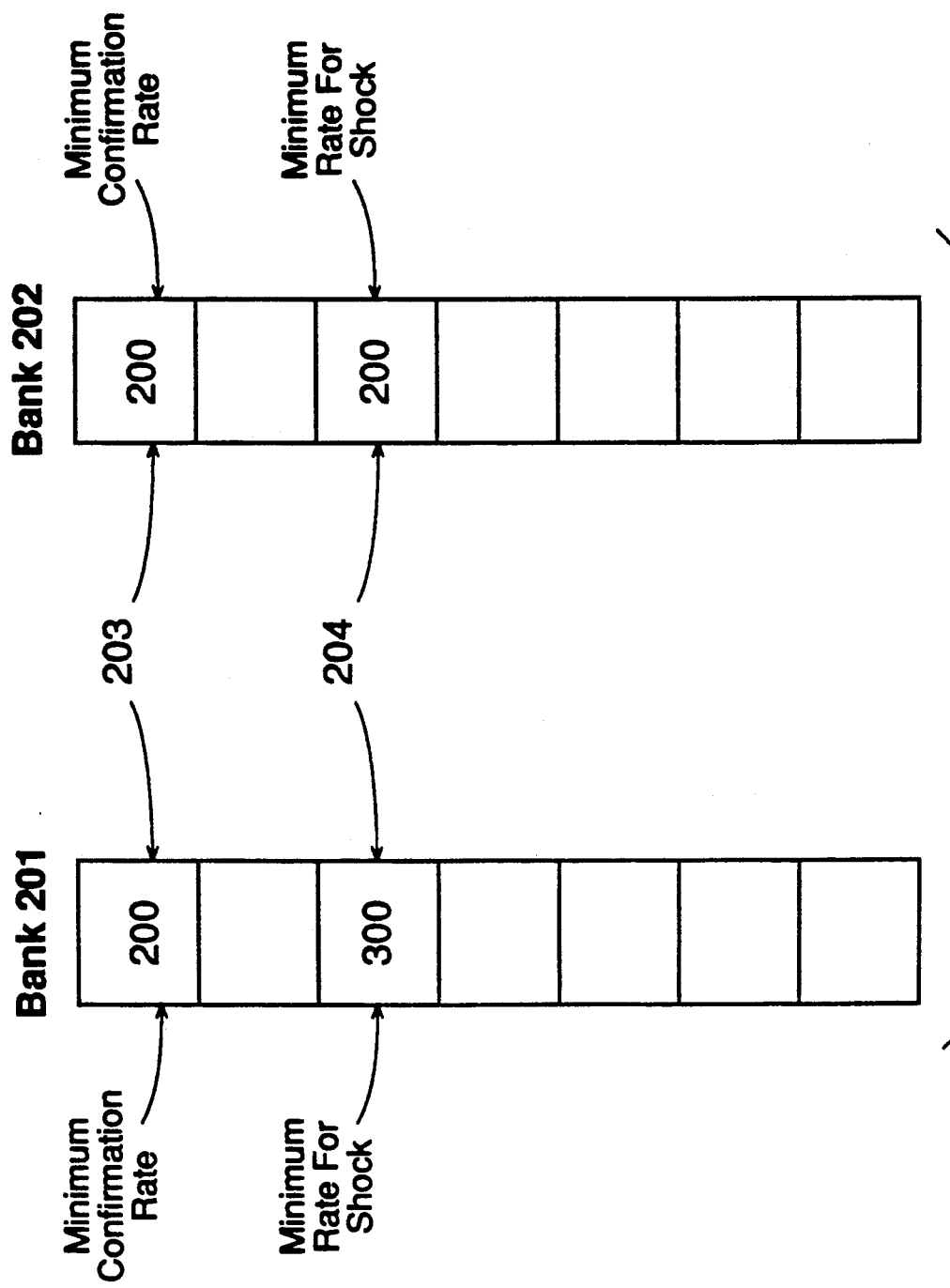

APPARATUS AND METHOD FOR CONTROLLING TACHYARRHYTHMIA CONFIRMATION IN RESPONSE TO PATIENT HISTORY

TECHNICAL FIELD

This invention relates generally to the field of implantable cardioverters/defibrillators (ICDs) and, more specifically, to ICDs which minimize the number of electrical shocks required to be delivered to the heart in order to revert arrhythmias.

DESCRIPTION OF THE PRIOR ART

ICDs are well known in the art and have been in widespread use for a number of decades. Typically, ICDs contain one or more sensing leads for sensing arrhythmias in the heart and for delivering appropriate electrical therapy in order to revert such arrhythmias. Such electrical therapy may include combinations of pacing pulses and shocks, depending upon what type of arrhythmia is in progress.

While electrical therapy is useful and indeed, in many cases lifesaving, it is by no means desirable or comfortable to deliver electrical shock to a patient. Consequently, most ICDs include a confirmation step in an attempt to minimize the number and energy of electrical shocks delivered to the patient's heart. More particularly, upon detection of an arrhythmia, the ICD configures itself to a "ready" state after which the shock will be delivered. Up to half a minute may elapse from detection of the arrhythmia to deliverance of the electrical therapy to the heart. Therefore, just prior to delivering the electrical therapy to the heart, the arrhythmia is confirmed. This process assures that if the arrhythmia spontaneously reverts between detection and confirmation, the ICD will not deliver the electrical therapy to the heart. Thus, unnecessary shock to the patient is avoided.

One drawback of prior arrangements is that there is only one set of confirmation parameters, typically the same as those used to detect the presence of the arrhythmia in the first place. If a slow arrhythmia is detected, and confirmed, electrical therapy will be delivered notwithstanding the fact that many patients can tolerate a slow arrhythmia for some time. Furthermore, if a fast arrhythmia is detected but between detection and confirmation, the arrhythmia has slowed, shock will be delivered although the arrhythmia has considerably subsided and may be in the process of reverting.

U.S. Pat. Nos. 4,969,465 to Pless, Ball and Fain and 4,971,058 to Pless, Ball, Fain and Luceri describe the use of different detection parameters. Specifically, one set of parameters is utilized to detect and confirm the presence of an arrhythmia, and another set of parameters is utilized to detect the presence of the arrhythmia after the appropriate electrical therapy is delivered to the heart. However, as in all other prior known arrangements, there is no provision for varying the parameters utilized to detect and confirm the arrhythmia before electrical therapy is delivered. Thus, the problem of confirming an arrhythmia which has already begun to spontaneously revert, or which may be tolerable to the patient for a finite time, is still present.

SUMMARY OF THE INVENTION

The above and other problems of the prior art are overcome in accordance with the present invention, which relates to a novel method and apparatus for detecting and confirming arrhythmias. In accordance with the invention, the threshold required to detect an arrhythmia is different from the threshold required to confirm said arrhythmia. In the preferred embodiment, there are two minimum heart rates utilized to confirm the arrhythmia. A first confirmation threshold, which indicates normal confirmation, results in electrical therapy being delivered to the heart. A second confirmation threshold indicates that while the arrhythmia is still present, no shock should be delivered. In this case, the arrhythmia is slow enough that it is tolerable for a predetermined time period. Therefore, shock is withheld and the arrhythmia is reconfirmed sometime later. If the arrhythmia is still present later, even though not severe, shock is delivered because even mild arrhythmias become dangerous after a while. Thus, the severity of the arrhythmia is used to determine whether to shock or to reconfirm.

By making this distinction, severe arrhythmias are immediately shocked, but mild arrhythmias are not. Rather, mild (tolerable) arrhythmias are allowed to continue in the hope that they will spontaneously revert. Only if after a predetermined time the mild arrhythmia has not reverted is a shock delivered.

As will be described hereafter, numerous other advantages are achieved by allowing the confirmation parameters utilized by the ICD to be varied, based upon combinations of one or more indicators such as/ length of time elapsed between confirmation and reconfirmation, condition of physical parameters such as blood pressure, or any other parameters deemed appropriate by the physician.

FIG. 1 is a block diagram of an implantable cardioverter defibrillator (ICD) in accordance with the present invention; and FIG. 2 shows two banks of parameters to be utilized by the ICD in delivering pacing therapy.

DETAILED DESCRIPTION OF THE PREFERRED EMBODIMENT

Figure 1:
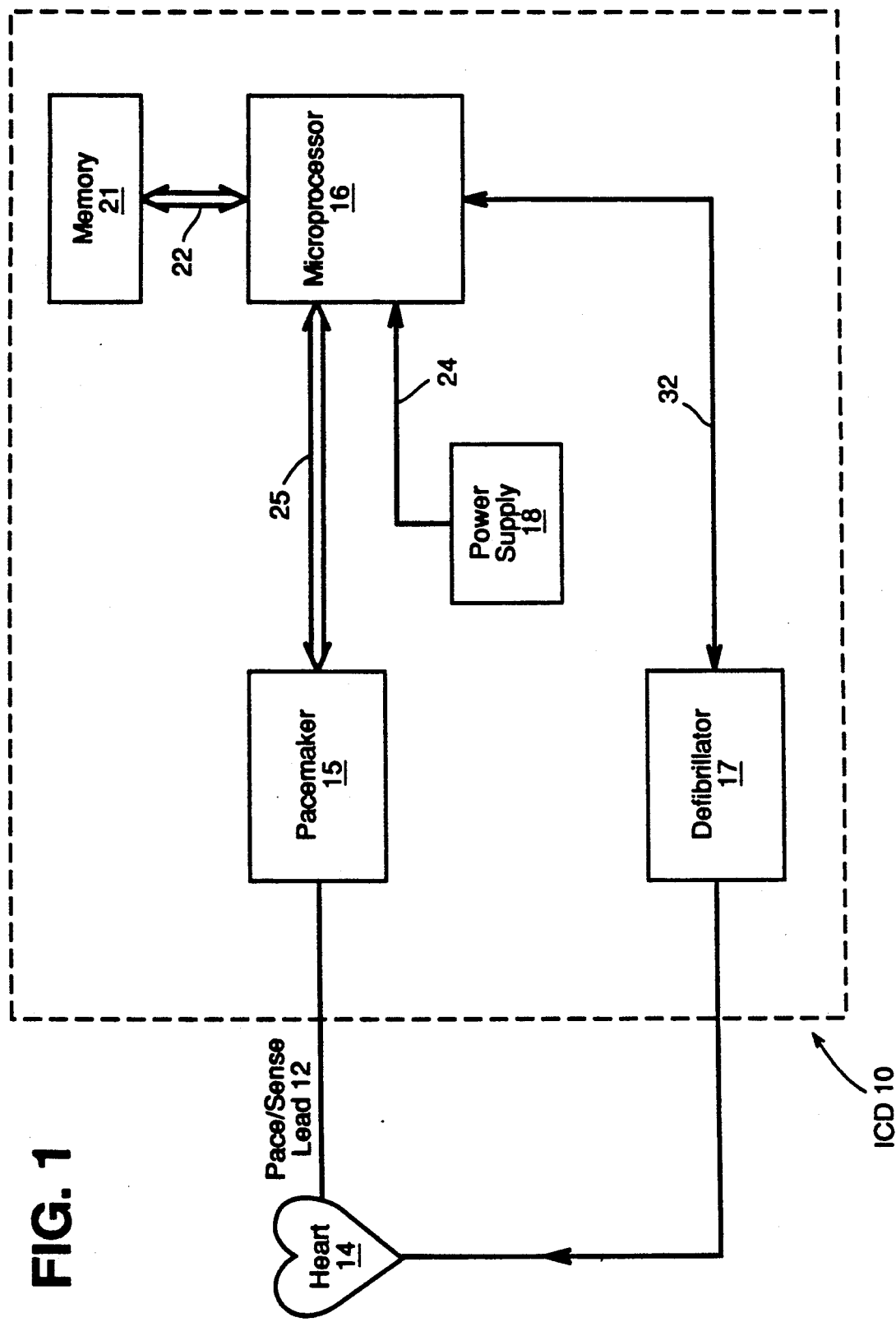

FIG. 1 shows a block diagram of a microprocessor controlled ICD 10 coupled to a patient's heart 14 for implementation of the invention. FIG. 1 comprises a conventional pacemaker 15, a memory 21, a power supply 18, a defibrillator 17 and a microprocessor 16. Various basic control and communication lines are shown interconnecting the key components of the system.

In operation, pacemaker 15 senses analog electrocardiac activity from the heart 14 via a lead 12 and detects the presence of an arrhythmia. Such detection is conveyed to microprocessor 16 via a communication bus 25. Memory 21 includes one or more sets of parameters, as described hereafter, which may be used to confirm the presence of the arrhythmia prior to delivering electrical therapy. The proper confirmation parameters are extracted from memory 21 and utilized by microprocessor 16 in conjunction with further signals received by pacemaker 15 for confirmation of the arrhythmia.

The ECG signal between detection of the arrhythmia an confirmation may be digitized by pacemaker 15 and forwarded to microprocessor 16 for analysis as is known in the art. Additionally, the sensitivity level used for detection may be different from that used for confirmation and the algorithms may even be different. For example, initial detection may be done utilizing analog components while confirmation may be done utilizing a digital signal processing arrangement.

Upon confirmation of the arrhythmia, microprocessor 16 may either instruct pacemaker 15 to deliver appropriate anti-tachycardia pacing or may issue a command to defibrillator 17 to shock the heart back into normal sinus rhythm. The details of the techniques for determining the pacing rate and for deciding between antitachycardia pacing or defibrillation shock may be accomplished in accordance with conventional techniques.

FIG. 2 shows two banks of parameters which may be implemented as electronic memory locations within the Implantable Cardioverter/Defibrillator (ICD) 10. Banks 201 and 202 ideally include identical parameters, although the programmed value of these parameters are independent. Several exemplary parameters which may be included in each of the banks are shown in FIG. 2. Several techniques for varying the values of these parameters in order to provide effective shock therapy to the patient while minimizing the number of unnecessary shocks delivered are described hereafter.

Consider a patient who can tolerate a slow tachyarrhythmia for a certain amount of time but thereafter cannot tolerate the slow tachyarrhythmia. The ICD installed in such a patient should, after detecting and confirming the arrhythmia, delay for some period of time before delivering any therapy. This is because the patient, as determined from electrophysiological testing, can tolerate the slow tachyarrhythmia for a particular time period. Therefore, the number of unnecessary shocks delivered to the patient can be minimized by permitting this time-out period to elapse in the hope that the arrhythmia may spontaneously revert during this time.

In accordance with the technique, bank 201 includes a minimum confirmation rate (MCR), stored in location 203, of 200 beats per minute. However, the minimum rate for shock (MRS) stored in location 204 of bank 201 is 300 beats per minute. The MCR and MRS parameters are both 200 in bank 202, as shown in FIG. 2. Numerous other memory locations are shown in FIG. 2. These may be used to store other parameters associated with the arrhythmia.

In operation, detection of an arrhythmia triggers the confirmation process within ICD 10 for confirming the arrhythmia. Specifically, after the arrhythmia is detected, shock capacitors begin to charge and a timer is started to determine when to perform the confirmation. Bank 201 shows that the arrhythmia will be initially confirmed if it is determined that the heart is beating at least 200 beats per minute. Other parameters may also be used to confirm the presence of the arrhythmia.

If the heart is beating between 200-300 beats per minute, the arrhythmia will be confirmed but shock will be withheld. A timer within microprocessor 16 will begin running and a period of time equal to the amount of time that the patient can tolerate the slow (200-300 beats/minute) tachyarrhythmia will begin to elapse. At the end of such time period, the arrhythmia will be reconfirmed utilizing the parameters from bank 202 this time. Since the MCR and MRS parameters in bank 202 are equal, confirmation of the presence of the arrhythmia after the required time period has elapsed will result in electrical therapy being delivered to the heart irrespective of whether or not the arrhythmia is a slow (200-300 BPM) or a fast (>300 BPM) tachyarrhythmia.

Since the minimum rate for shock is less in bank 202 than in bank 201, anti-tachyarrhythmia shock therapy will become more aggressive as the length of time during which the arrhythmia is present increases. In other words, the second bank of parameters will result in shock being delivered to all arrhythmias to which the first bank would deliver, as well as other arrhythmias which the first bank would confirm but not shock. Since all parameters in the two banks are programmable, it may be desirable to include an error check algorithm within microprocessor 16 to guarantee that the minimum rate for shock in bank 202 is never greater than that in bank 201; i.e., that the second bank of parameters is stricter than the first. It is noted that some patients may be able to tolerate very slow arrhythmias for extremely long periods of time. This can be compensated for by making the time-out period discussed above extremely large.

It is also noted that, while two exemplary banks, 201 and 202, are utilized for purposes of explanation, multiple banks may be used. For example, it may be determined that a first set of parameters should be used to initially confirm the arrhythmia, a second set of parameters should be used after a specified time-out period, and still another set should be used after an even longer delay. Moreover, rather than switching among banks of parameters based upon a time period elapsing, other indicators can be used to select the proper bank of parameters. For example, a physical parameter of the patient, such as blood pressure, could be measured and used to determine which bank of parameters would be most effective. A system could be configured which will normally wait a predetermined time period to reconfirm but which will reconfirm and shock before the end of that period if the patient's blood pressure falls below a critical value.

The delivery of a cardioversion/defibrillation shock also can be used to switch parameters, as can the history of the patient, the detection of fault conditions in the pacing circuit itself, or any other control parameters. Indeed, the parameters may even be used in combination. For example, it could be determined that three banks would be utilized—the first bank to initially confirm the arrhythmia and determine if shock is necessary, the second bank utilized after a certain amount of time if shock has not been delivered during the process of utilizing the first bank of parameters, and a third bank of parameters being utilized after the same amount of time elapsed from utilization of the first bank, but only if cardioversion/defibrillation therapy has already been delivered. Various combinations and/or variations can be determined by the physician in accordance with electrophysiological examination and, in particular, patient needs, responses, tolerances for slow and fast arrhythmias, and ability to withstand electrical shocks.

It is also preferable that bradycardia support pacing be inhibited for programmable periods of time after antitachycardia pacing or defibrillation which reverts a tachyarrhythmia so as to avoid any pro-arrhythmic effect. The use of such a delay is described in U.S. Pat. No. 4,940,054, entitled "APPARATUS AND METHOD FOR CONTROLLING MULTIPLE SENSITIVITIES IN ARRHYTHMIA CONTROL SYSTEM INCLUDING POST THERAPY PACING DELAY," to Richard Grevis and Norma L. Gilli. The time limit for the application of antitachyarrhythmia therapy is of importance. In this regard, reference is made to U.S. Pat. No. 4,895,151 to Richard Grevis and Loraine Holley, entitled "APPARATUS AND METHOD FOR THERAPY ADJUSTMENT IN IMPLANTABLE CARDIOVERTER," which is hereby incorporated by reference.

The above describes the preferred embodiment of the invention. It is understood that other variations may be implemented by those of ordinary skill in the art. For example, the pacing may be delivered to the atrium, the ventricle, or to both the atrium and the ventricle. Additionally, the microprocessor may be replaced with hardwired logic, or implemented directly within the pacemaker 15.

What is claimed is:

1. Apparatus for delivering electrical therapy to a heart for reverting an arrhythmia, said apparatus comprising:
    means for detecting the presence of the arrhythmia;
    first means responsive to detection of an arrhythmia by said detecting means for comparing characteristics of said arrhythmia to a first set of parameters to confirm said arrhythmia;
    means for delivering electrical therapy to the heart;
    means for activating said electrical therapy delivering means to revert the arrhythmia if said first comparing means indicates that the severity of the arrhythmia is greater than a predetermined threshold, and for withholding deliverable of electrical therapy if said arrhythmia is confirmed but the severity of said arrhythmia is not beyond said predetermined threshold;
    second means, responsive to said confirmation, for comparing characteristics of said arrhythmia to a second set of parameters to reconfirm said arrhythmia, said first and second sets of parameters being different from each other; and
    means for activating said electrical therapy delivering means if said arrhythmia is reconfirmed.

2. Apparatus according to claim 1, wherein said predetermined threshold is a specified number of beats per minute.

3. Apparatus according to claim 1, wherein said means for reconfirming is arranged to reconfirm said arrhythmia a predetermined time period after said arrhythmia is confirmed.

4. Apparatus according to claim 1, wherein said means for reconfirming is arranged to reconfirm said arrhythmia either a predetermined time after said arrhythmia is confirmed or when the patient's blood pressure falls below a predetermined value, whichever occurs first.

5. Apparatus according to claim 1, further comprising means for assuring that said second set of parameters is stricter than said first set so that said second comparing means reconfirms the presence of an arrhythmia for less severe arrhythmias than those confirmed by said first comparing means.

6. Apparatus according to claim 1, wherein said electrical therapy is delivered to a portion of the heart selected from a group including an atrium, a ventricle, and both an atrium and a ventricle.

7. A method of delivering electrical therapy to a heart for reverting an arrhythmia, said method comprising the steps of:
    detecting the presence of the arrhythmia;
    in response to said step of detecting, comparing characteristics of said arrhythmia to a first set of parameters to confirm said arrhythmia;
    delivering electrical therapy to the heart to revert the arrhythmia if said step of comparing indicates that the severity of the arrhythmia is greater than a predetermined threshold, and withholding deliverance of electrical therapy if said arrhythmia is confirmed but the severity of said arrhythmia is not beyond said predetermined threshold;
    in response to confirmation of an arrhythmia, comparing characteristics of said arrhythmia to a second set of parameters to reconfirm said arrhythmia, said first and second sets of parameters being different from each other; and
    delivering electrical therapy to the heart to revert the arrhythmia if said arrhythmia is reconfirmed.

8. A method according to claim 7, wherein said predetermined threshold is a specified number of beats per minute.

9. A method according to claim 7, wherein said step of reconfirming reconfirms said arrhythmia a predetermined time period after said arrhythmia is confirmed.

10. A method according to claim 7, wherein said step of reconfirming reconfirms said arrhythmia either a predetermined time after said arrhythmia is confirmed or when the patient's blood pressure falls below a predetermined value, whichever occurs first.

11. A method according to claim 7, further comprising the step of assuring that said second set of parameters is stricter than said first set so that said second comparing step reconfirms the presence of an arrhythmia for less severe arrhythmias than those confirmed by said first comparing step.

12. A method according to claim 7, wherein said electrical therapy is delivered to a portion of the heart selected from a group including an atrium, a ventricle, and both an atrium and a ventricle.

* * * * *